US008784337B2

(12) United States Patent
Voeller et al.

(10) Patent No.: US 8,784,337 B2
(45) Date of Patent: *Jul. 22, 2014

(54) CATHETER WITH AN IMPROVED FLEXURAL RIGIDITY PROFILE

(71) Applicant: Boston Scientific Scimed, Inc., Maple Grove, MN (US)

(72) Inventors: Virgil F. Voeller, St. Louis Park, MN (US); Clay Northrop, Salt Lake City, UT (US); Ted Layman, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/048,852

(22) Filed: Oct. 8, 2013

(65) Prior Publication Data

US 2014/0052107 A1 Feb. 20, 2014

Related U.S. Application Data

(63) Continuation of application No. 13/077,579, filed on Mar. 31, 2011, now Pat. No. 8,551,021.

(60) Provisional application No. 61/319,720, filed on Mar. 31, 2010.

(51) Int. Cl.
*A61B 5/00* (2006.01)

(52) U.S. Cl.
USPC .......................................................... 600/585

(58) Field of Classification Search
CPC ............ A61M 25/09; A61M 25/0053; A61M 25/0054; A61M 2025/0915; A61M 2025/09108

USPC .......................................................... 600/585
See application file for complete search history.

(56) References Cited

U.S. PATENT DOCUMENTS 1,553,227 A 9/1925 Anton et al.
1,866,888 A 7/1932 Hawley
(Continued)

FOREIGN PATENT DOCUMENTS

EP 0 215 173 3/1987
EP 0 377 453 7/1990
(Continued)

OTHER PUBLICATIONS

H.A. Rothbart, "Helical Compression Springs", Mechanical Design and Systems Handbook, 1964, p. 33-13 (one sheet).

*Primary Examiner* — Max Hindenburg
(74) *Attorney, Agent, or Firm* — Seager, Tufte & Wickhem, LLC

(57) ABSTRACT

Medical devices and methods for making and using the same are disclosed. An example medical device may include a guidewire. The guidewire may include a core wire having a distal portion. A tubular member may be disposed over the distal portion. The tubular member may have a plurality of slots formed therein and may have a longitudinal axis. The tubular member may include a variably spaced slot section that has a flexural rigidity that varies from a first flexural rigidity to a second flexural rigidity. The transition from the first flexural rigidity to the second flexural rigidity may be a function of a fourth power equation. The first flexural rigidity may be in the range of about $1\times10^{-6}$ to about $9\times10^{-5}$ lbs-inches$^2$. The second flexural rigidity may be in the range of about $1\times10^{-3}$ to about $5\times10^{-3}$ lbs-inches$^2$.

20 Claims, 8 Drawing Sheets

(56) References Cited

U.S. PATENT DOCUMENTS

| | | |
|---|---|---|
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,538,622 A | 9/1985 | Samson et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gambale |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,228,453 A | 7/1993 | Sepetka |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,049 A | 11/1994 | Raman et al. |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,409,015 A | 4/1995 | Palermo |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |

(56) References Cited

U.S. PATENT DOCUMENTS

| | | |
|---|---|---|
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,605,543 A | 2/1997 | Swanson |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,664,580 A | 9/1997 | Erickson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita et al. |
| 5,897,537 A | 4/1999 | Berg et al. |
| 5,902,254 A | 5/1999 | Magram |
| 5,902,290 A | 5/1999 | Peacock, III et al. |
| 5,902,499 A | 5/1999 | Richerzhagen |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,955,640 A | 9/1999 | Paludetto et al. |
| 5,971,975 A | 10/1999 | Mills et al. |
| 5,980,471 A | 11/1999 | Jafari |
| 5,997,487 A | 12/1999 | Kolehmainen et al. |
| 6,001,068 A | 12/1999 | Uchino et al. |
| 6,004,279 A | 12/1999 | Crowley et al. |
| 6,007,478 A | 12/1999 | Siess et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,071,305 A | 6/2000 | Brown et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 * | 12/2001 | Trotta ............ 604/523 |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,383,146 B1 | 5/2002 | Klint |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 | 6/2003 | Jacobsen et al. |
| 6,602,207 B1 | 8/2003 | Mann et al. |
| 6,602,280 B2 | 8/2003 | Chobotov |
| 6,610,046 B1 | 8/2003 | Usami et al. |

(56) References Cited

U.S. PATENT DOCUMENTS

| | | |
|---|---|---|
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,673,025 B1 | 1/2004 | Richardson et al. |
| 6,682,493 B2 | 1/2004 | Mirigian |
| 6,689,120 B1 | 2/2004 | Gerdts |
| 6,702,762 B2 | 3/2004 | Jafari et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |
| 7,153,277 B2 | 12/2006 | Skujins et al. |
| 7,169,118 B2 | 1/2007 | Reynolds et al. |
| 7,182,735 B2 | 2/2007 | Shireman et al. |
| 7,618,379 B2 | 11/2009 | Reynolds et al. |
| 7,850,623 B2 | 12/2010 | Griffin et al. |
| 7,878,984 B2 | 2/2011 | Davis et al. |
| 7,905,913 B2 | 3/2011 | Chew et al. |
| 7,914,466 B2 | 3/2011 | Davis et al. |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0111044 A1 | 6/2004 | Davis et al. |
| 2004/0116831 A1 | 6/2004 | Vrba |
| 2004/0142643 A1 | 7/2004 | Miller et al. |
| 2004/0167437 A1 | 8/2004 | Sharrow et al. |
| 2004/0167441 A1 | 8/2004 | Reynolds et al. |
| 2004/0181176 A1 | 9/2004 | Jafari et al. |
| 2005/0115624 A1 | 6/2005 | Walak |
| 2006/0121218 A1 | 6/2006 | Obara et al. |
| 2006/0122537 A1 | 6/2006 | Reynolds et al. |
| 2006/0264904 A1 | 11/2006 | Kerby et al. |
| 2007/0100374 A1 | 5/2007 | Vrba |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0064989 A1 | 3/2008 | Chen et al. |
| 2008/0077119 A1 | 3/2008 | Snyder et al. |
| 2009/0043283 A1 | 2/2009 | Turnlund et al. |
| 2009/0043372 A1 | 2/2009 | Northrop et al. |
| 2009/0118675 A1 | 5/2009 | Czyscon et al. |
| 2009/0177185 A1 | 7/2009 | Northrop |
| 2009/0254000 A1 | 10/2009 | Layman et al. |
| 2010/0063479 A1 | 3/2010 | Merdan et al. |
| 2011/0245808 A1 | 10/2011 | Voeller et al. |

FOREIGN PATENT DOCUMENTS

| | | |
|---|---|---|
| EP | 0 778 039 | 6/1997 |
| EP | 0 937 481 | 8/1999 |
| EP | 0 790 066 | 4/2000 |
| EP | 0 608 853 | 4/2003 |
| GB | 2257269 | 1/1993 |
| JP | 58-8522 | 1/1983 |
| JP | 62-299277 | 12/1987 |
| JP | 1-135363 | 5/1989 |
| JP | 1-158936 | 6/1989 |
| JP | 2-107268 | 4/1990 |
| JP | 3-122850 | 12/1991 |
| JP | 4-061840 | 2/1992 |
| JP | 5-506806 | 10/1993 |
| JP | 5-309519 | 11/1993 |
| JP | 6-31749 | 4/1994 |
| JP | 6-63224 | 9/1994 |
| JP | 6-312313 | 11/1994 |
| JP | 7-124164 | 5/1995 |
| JP | 7-124263 | 5/1995 |
| JP | 7-136280 | 5/1995 |
| JP | 7148264 | 6/1995 |
| JP | 7037199 | 7/1995 |
| JP | 7185009 | 7/1995 |
| JP | 7275366 | 10/1995 |
| JP | 751067 | 11/1995 |
| JP | 8509141 | 10/1996 |
| JP | 8-317988 | 12/1996 |
| JP | 9-000164 | 4/1997 |
| JP | 9-276413 | 10/1997 |
| JP | 10-118193 | 5/1998 |
| JP | 2000-197704 A | 7/2000 |
| WO | WO 90/02520 | 3/1990 |
| WO | WO 95/32834 | 12/1995 |
| WO | WO 96/38193 | 12/1996 |
| WO | WO 97/44086 | 11/1997 |
| WO | WO 99/11313 | 3/1999 |
| WO | WO 02/13682 | 2/2002 |
| WO | WO 2004/047899 | 6/2004 |

* cited by examiner

CATHETER WITH AN IMPROVED FLEXURAL RIGIDITY PROFILE

CROSS-REFERENCE TO RELATED PUBLICATIONS

This application is a continuation of U.S. application Ser. No. 13/077,579, filed Mar. 31, 2011, now U.S. Pat. No. 8,551,021; which claims priority under 35 U.S.C. §119 to U.S. Provisional Application Ser. No. 61/319,720, filed Mar. 31, 2010, the entire disclosures of which are incorporated herein by reference.

FIELD OF THE INVENTION

The present invention pertains to medical devices, and methods for manufacturing medical devices. More particularly, the present invention pertains to elongated medical devices including a slotted tubular member, components thereof, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

Embodiments of the present disclosure provide design, material, manufacturing method, and use alternatives for medical devices and tubular members for use in medical devices. An example medical device may include a guidewire. The guidewire may include a core wire having a distal portion. A tubular member may be disposed over the distal portion. The tubular member may have a plurality of slots formed therein and may have a longitudinal axis. The tubular member may include a variably spaced slot section that has a flexural rigidity that varies from a first flexural rigidity to a second flexural rigidity. The transition from the first flexural rigidity to the second flexural rigidity may be a function of a fourth power equation. The first flexural rigidity may be in the range of about $1 \times 10^{-6}$ to about $9 \times 10^{-5}$ lbs-inches$^2$. The second flexural rigidity may be in the range of about $1 \times 10^{-3}$ to about $5 \times 10^{-3}$ lbs-inches$^2$.

Another example guidewire may include a linear-elastic nickel-titanium core wire having a distal portion. A super-elastic nickel-titanium tubular member may be disposed over the distal portion. The tubular member may have a plurality of slots formed therein and may have a longitudinal axis. The tubular member may include a variably spaced slot section that has a flexural rigidity that varies from a first flexural rigidity to a second flexural rigidity. The transition from the first flexural rigidity to the second flexural rigidity may be a function of a fourth power equation. The first flexural rigidity may be in the range of about $1 \times 10^{-6}$ to about $9 \times 10^{-5}$ lbs-inches$^2$. The second flexural rigidity may be in the range of about $1 \times 10^{-3}$ to about $5 \times 10^{-3}$ lbs-inches$^2$.

An example method for manufacturing a guidewire may include providing a tubular member having a longitudinal axis, forming a first slot in the tubular member at a first position along the longitudinal axis, forming a second slot in the tubular member at a second position along the longitudinal axis, and forming a plurality of additional slots in the tubular member at a plurality of positions along the longitudinal axis. The first slot, the second slot, and the plurality of additional slots may be variably spaced along the longitudinal axis of the tubular member so as to define a variably spaced slot section that has a flexural rigidity that varies from a first flexural rigidity to a second flexural rigidity. The transition from the first flexural rigidity to the second flexural rigidity may be a function of a fourth power equation. The first flexural rigidity may be in the range of about $1 \times 10^{-6}$ to about $9 \times 10^{-5}$ lbs-inches$^2$. The second flexural rigidity may be in the range of about $1 \times 10^{-3}$ to about $5 \times 10^{-3}$ lbs-inches$^2$.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The devices and methods of the present disclosure may be more completely understood in consideration of the following detailed description of various embodiments in connection with the accompanying drawings, in which.

Figure 1:
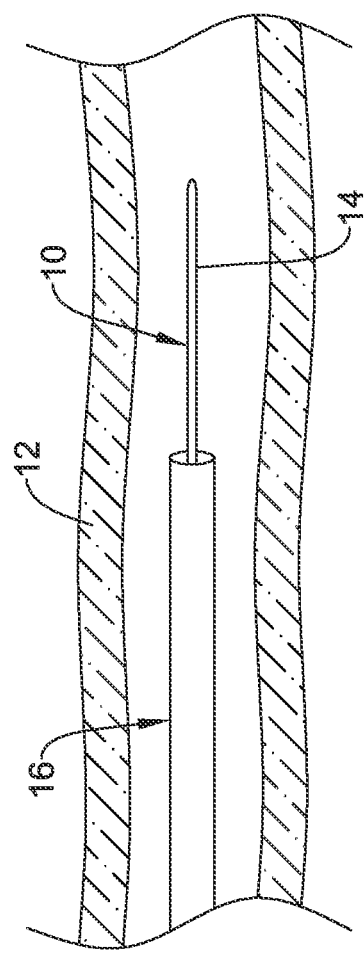
FIG. 1 is a plan view of an example medical device disposed in a blood vessel.

While the embodiments described herein are amenable to various modifications and alternative forms, specifics thereof have been shown by way of example in the drawings and will be described in detail. It should be understood, however, that the intention is not to limit the devices and methods to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
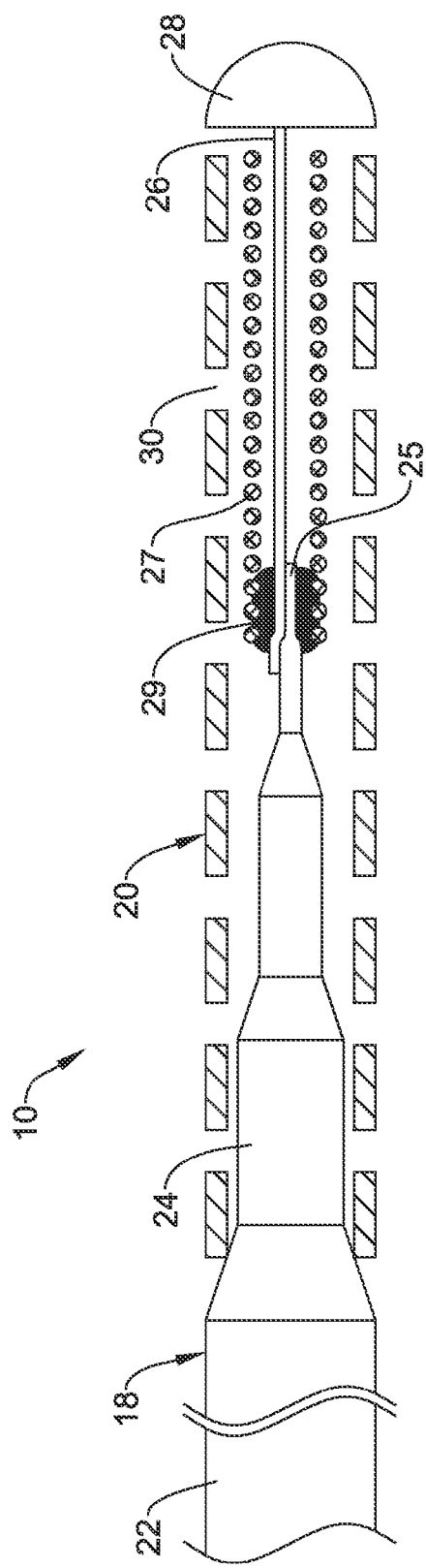
FIG. 2 is a partial cross-sectional side view of an example medical device.

FIG. 2 is a partial cross-sectional view of guidewire 10. It can be seen that guidewire 10 may include a core member or core wire 18 and a tubular member 20 disposed over at least a portion of core wire 18. Tubular member 20 may have a plurality of slots 30 formed therein. Core wire 18 may include a proximal section 22 and a distal section 24. A connector (not shown) may be disposed between and attach proximal section 22 to distal section 24. Alternatively, core wire 18 may be a unitary member without a connector. A shaping member 26 may be coupled to core wire 18 (for example distal section 24 of core wire 18), tubular member 20, or both. Shaping member 26 may be made from a relatively inelastic material so that a clinician can bend or shape the distal end of guidewire 10 into a shape that may facilitate navigation of guidewire 10 through the anatomy. Some examples of suitable materials for core wire 18, tubular member 20, shaping member 26, etc. can be found herein. A coil 27, for example a radiopaque coil, may be disposed over core wire 18 and shaping member 26. A solder bond 29 may join core wire 18, shaping member 26, and coil 27. Other joining structures and/or methods are contemplated. A tip member 28 may also be coupled to core wire 18, tubular member 20, or both that may define an atraumatic distal tip of guidewire 10. In general, tip member 28 may include solder. However, other versions of tip member 28 are contemplated including tip members 28 that comprise or form a polymeric tip.

Core wire 18, for example distal section 24 of core wire 18, may include one or more tapers or tapered sections and a flattened or stamped distal end 25. Core wire 18 may also include one or more constant outer diameter sections. The tapers or tapered sections may be formed by a number of different techniques, for example, by centerless grinding methods, stamping methods, and the like. The centerless grinding technique may utilize an indexing system employing sensors (e.g., optical/reflective, magnetic) to avoid excessive grinding of the core wire 18 section. In addition, the centerless grinding technique may utilize a CBN or diamond abrasive grinding wheel that is well shaped and dressed to avoid grabbing core wire 18 during the grinding process. In some embodiments, core wire 18 is centerless ground using a Royal Master HI-AC centerless grinder to define one or more tapered sections. In some embodiments, core wire 18 is ground using a CNC profile grinder to define one or more tapered sections.

Figure 3:
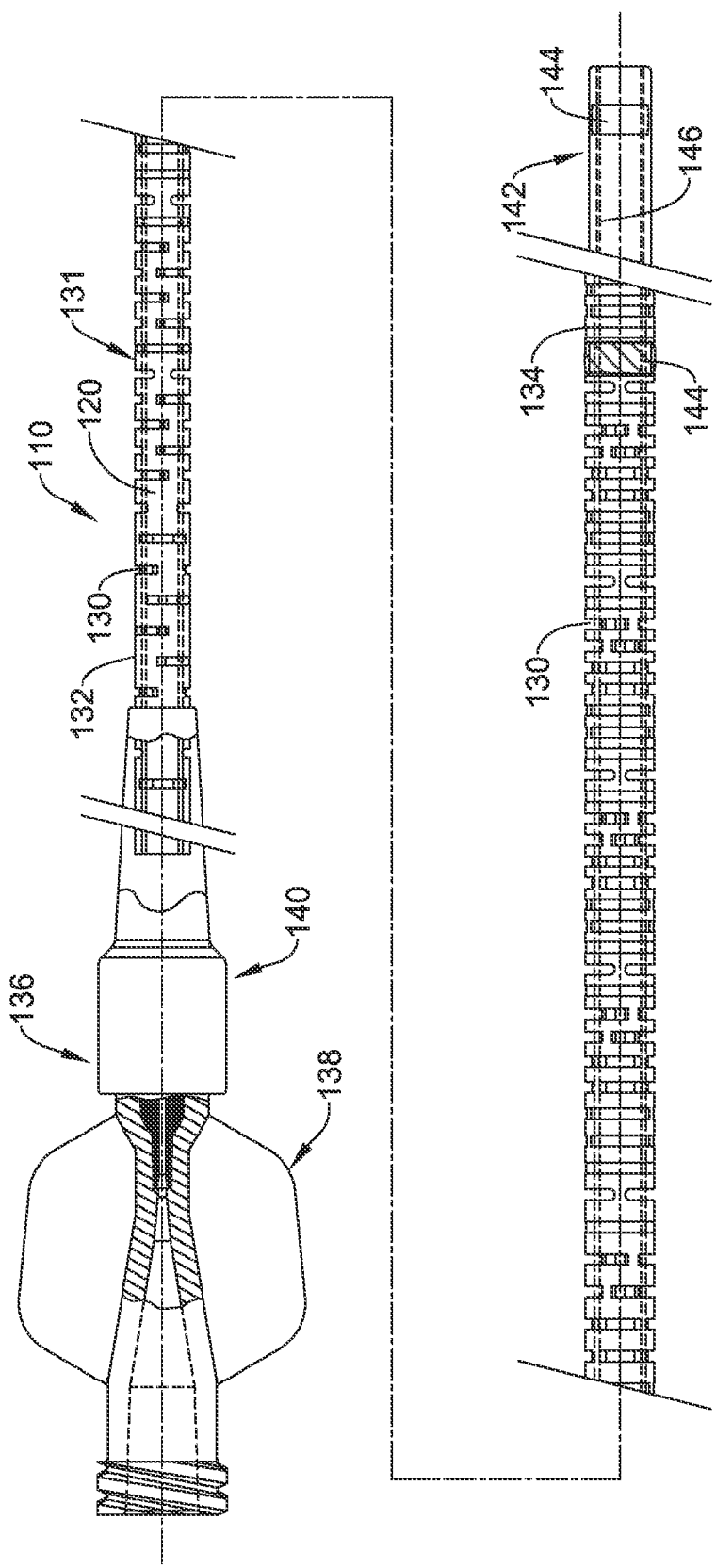
FIG. 3 is a partial cross-sectional side view of another example medical device.

Although medical device 10 is depicted in FIG. 1 as a guidewire, it is not intended to be limited to just being a guidewire. Indeed, medical device 10 may take the form of other suitable guiding, diagnosing, or treating device (including catheters, endoscopic instruments, laparoscopic instruments, etc., and the like) and it may be suitable for use at other locations and/or body lumens within a patient. For example, FIG. 3 illustrates another example device 110 in the form of a catheter. Catheter 110 may include a generally elongate shaft 131 having a proximal portion 132 and a distal portion 134. A proximal manifold 136 may be disposed at proximal portion 132. Manifold 136 may include a hub 138 and strain relief 140. A tip member 142 may be disposed at distal portion 134. Tip member 142 may include a radiopaque marker member 144. One or more additional marker members 144 may be disposed along other portions of catheter 110, for example along distal portion 134 of shaft 131. Shaft 131 may include a tubular member 120 that may be similar in form and function to other tubular members disclosed herein including tubular member 20 illustrated, for example, in FIG. 2. Tubular member 120 may have a plurality of slots 130 formed therein. A liner 146 may be disposed within tubular member 120. Liner 146 may be similar to an analogous structure disclosed in U.S. Pat. No. 7,001,369 and U.S. Patent Application Publication No. US 2006/0264904, the entire disclosures of which are herein incorporated by reference. Discussion herein pertaining to tubular member 20 and/or guidewire 10 (e.g., as illustrated in FIG. 2) may also be applicable to tubular member 120 and catheter 110, to the extent applicable.

Because of their intended use in the vasculature, some medical devices are designed to have particular physical characteristics such as flexibility (e.g., for the purposes of this disclosure, flexibility may be also be termed or expressed as bending stiffness or flexural rigidity). For example, medical devices may be designed to be flexible enough in order to bend in a manner sufficient to traverse the tortuous anatomy. At the far distal end of the medical device, it may be desirable to tailor the flexibility of the medical device so that the device can effectively reach its target within the vasculature. For example, in order to reach coronary vessels and/or vessels near the heart, which may have bends, or "take-offs" with angles of 90° or more, a guidewire may be designed to be quite flexible at the distal end. However, if the flexibility is too great, the guidewire may not efficiently turn at these take-offs and, instead, may have a tendency to buckle upon itself. Thus, tailoring the flexibility at the distal end of a guidewire (e.g., within about the first four to six inches or so of the guidewire) so that it is able to efficiently advance through coronary artery take-offs while minimizing the likelihood that the guidewire will buckle back upon itself may be desirable.

Figure 4:
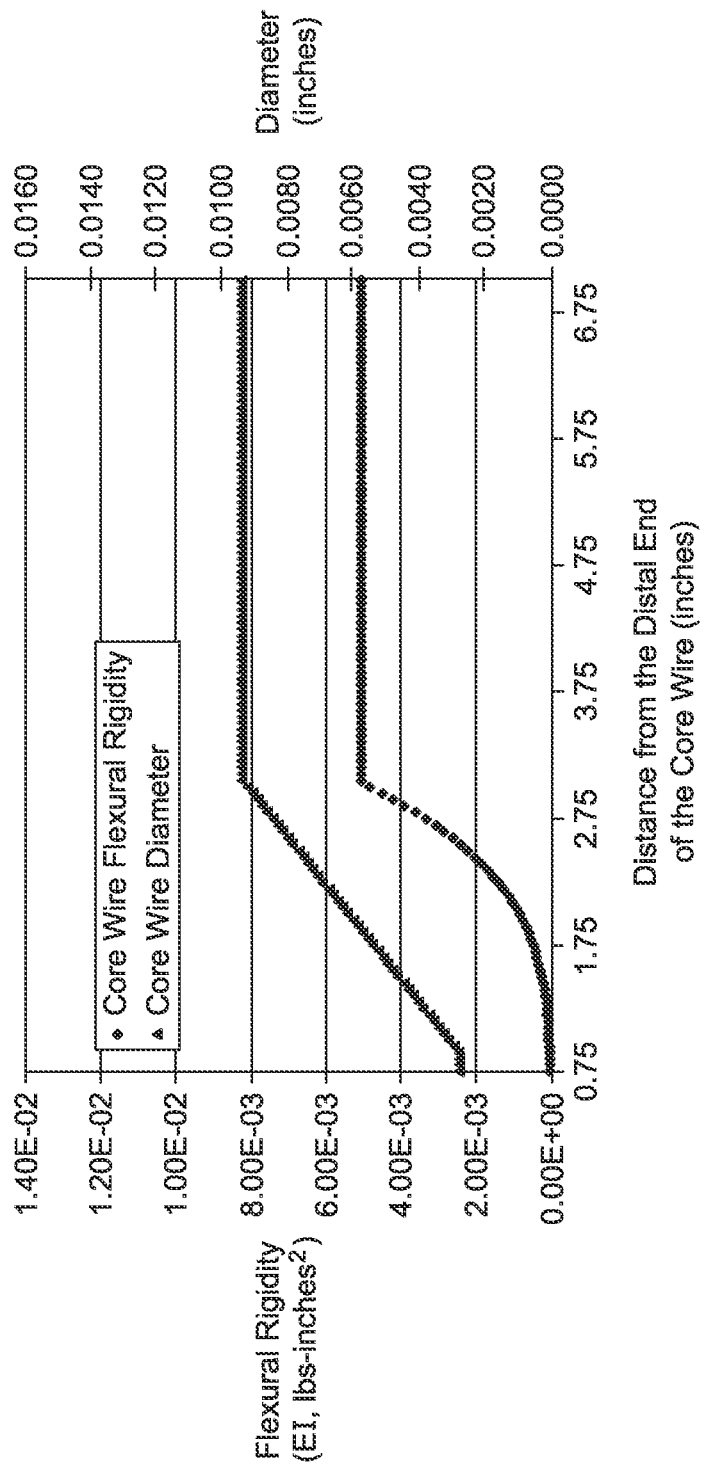
FIG. 4 is graph showing the changes in flexural rigidity and changes in diameter of a core wire relative to the distance from the distal end of the core wire.

When designing guidewires, such as polymer tip and/or spring tip guidewires, the core wire may be the major contributor to the overall flexural rigidity of the guidewire. Because the flexural rigidity of core wire may be a function of the diameter of the core, it may be desirable to taper or otherwise size the core wire so that it provides a desired flexural rigidity to the guidewire, for example at the distal end. For example, FIG. 4 is a graph illustrating the flexural rigidity of a core wire and the diameter of the core wire plotted versus the distance from the distal end of the core wire. The scale on the left side of the graph is the flexural rigidity in lbs-inch$^2$, defined as EI where E is Young's modulus of the core wire material (in this example, a stainless steel core wire), I is the area moment of inertia (because the core wire has a round cross-section, the area moment of inertia is $\pi r^4/4$ where r is the radius of the core wire). The scale on the right side of the graph is the diameter of the core wire in inches. The scale at the bottom of the graph is the distance from the distal end of the core wire in inches.

What can be seen in this graph is that a linear taper or transition in diameter of the core wire results in a non-linear change in flexural rigidity. Indeed, a linear taper in the core wire may provide a change in flexural rigidity that follows a non-linear transition that may be defined by a fourth order equation. Stated another way, the change in the flexural rigidity may be a function of a fourth order polynomial. Such a change in flexural rigidity may be desirable because it may provide the core wire with sufficient flexibility to traverse the vasculature and navigate coronary artery take-offs, yet be sufficiently resistant to buckling.

While coronary guidewires having such core wires may have desirable flexibility characteristics, they may not fully transmit torque from the proximal end to the distal end of the guidewire. This may limit a clinician's ability to accurately navigate the guidewire to its intended destination. One way to enhance the torquability in a guidewire may be to include a tubular member about a portion of a core wire such as tubular member 20, illustrated in FIG. 2, which may efficiently transmit torque along its length. Because tubular member 20 may include slots 30, it also may be highly flexible. Thus, the combination of a highly flexible core wire (e.g., core wire 18) and a highly flexible tubular member (e.g., tubular member 20) may result in a guidewire with desirable flexibility and torque-transmitting characteristics (e.g., guidewire 10).

Unlike in polymer tip and spring tip guidewires, where the polymeric material and springs coils in the tips may only contribute a negligible amount to the overall flexural rigidity of the guidewire, the structure of tubular member 20 may be such that it does contribute to the overall flexural rigidity of guidewire 10. Therefore, the flexural rigidity of core wire 18 alone may not determine the overall flexural rigidity of guidewire 10. Because of this, it may be desirable to tailor the flexural rigidity of tubular member 20 so that tubular member 20 can help contribute to the flexural rigidity of guidewire 10 in a manner that allows guidewire 10 to still efficiently traverse the vasculature while having a tendency to resist buckling.

Tubular member 20 may be fabricated in such a manner that it provides guidewire 10 with desirable flexural rigidity characteristics. For example, tubular member 20 may designed so that its flexural rigidity changes in a non-linear manner. This may include a change in flexural rigidity that follows a third order to a fifth order equation or, stated another way, is a function of a third order to a fifth order polynomial (e.g., is based on a mathematical equation that is a third order to a fifth order polynomial). For example, the flexural rigidity of the tubular member 20 may follow or otherwise be a function of a fourth order polynomial. This fourth order transition in flexural rigidity may take place along the entire length of tubular member 20 or it may occur in one or more sections of tubular member 20. For example, the flexural rigidity of tubular member 20 may follow a fourth order transition across the entire length of tubular member, across about the first five inches or so of tubular member 20, or in a section of tubular member 20 located along a portion of the first four inches or so of tubular member 20.

As indicated above, in some examples, the flexural rigidity of tubular member 20 may transition according to a fourth power equation or polynomial. Fourth power equations are a subset of fourth order equations or polynomials where the lower power coefficients are zero. Thus, a fourth power equation for flexural rigidity may be represented by the following equation:

$$FR(x)=A+Bx^4$$

where:

FR is the flexural rigidity,

A is the flexural rigidity at the start of the transition,

B is (the flexural rigidity at the end of the transition—the flexural rigidity at the start of the transition)/(length of the transition)$^4$, and x is the position along the transition and is defined as 0 at the start of the transition.

Thus, the flexural rigidity in tubular member 20 may transition across a transition length from a starting flexural rigidity to an ending flexural rigidity, and this transition may be a function of a fourth power equation.

Figure 5:
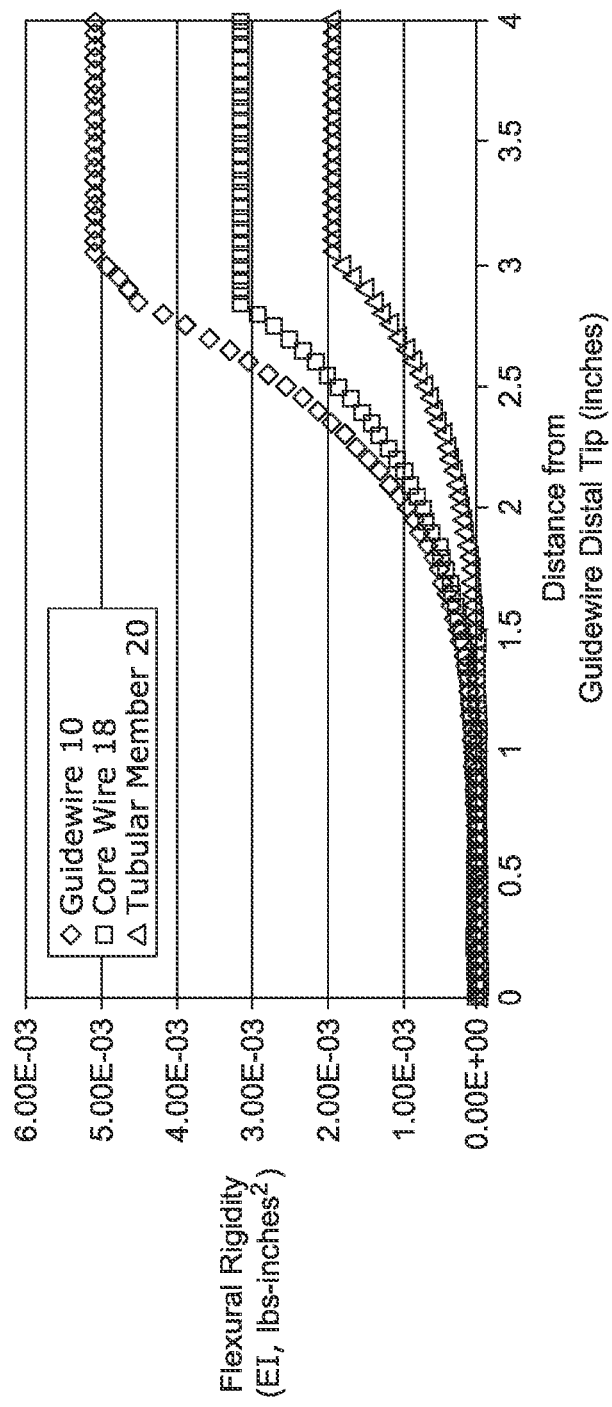
FIG. 5 is graph showing the changes in flexural rigidity in an example core wire, an example tubular member, and a guidewire relative to the distance from the distal end of the example guidewire.

FIG. 5 is a graph depicting flexural rigidity (flexural rigidity, FR, in lbs-inch$^2$) for core wire 18, tubular member 20, and guidewire 10. The scale at the bottom of the graph is the distance from the distal end of guidewire 10 in inches. Here it can be seen that flexural rigidity of core wire 18 changes in a non-linear manner. For example, the flexural rigidity of core wire 18 may be a function of a fourth order polynomial. Tubular member 20 also has a non-linear change in flexural rigidity and this change may be a function of a fourth order polynomial (e.g., a fourth order polynomial). The overall flexural rigidity of guidewire 10 may be essentially the sum of the flexural rigidity of core wire 18 and tubular member 20 and it changes in a non-linear manner (e.g., may be a function of a fourth order polynomial). Such flexibility characteristics may be desirable and may provide guidewire 10 with flexibility characteristics that allow guidewire 10 to traverse the vasculature and navigate coronary artery take-offs, yet be sufficiently resistant to buckling.

Figure 6:
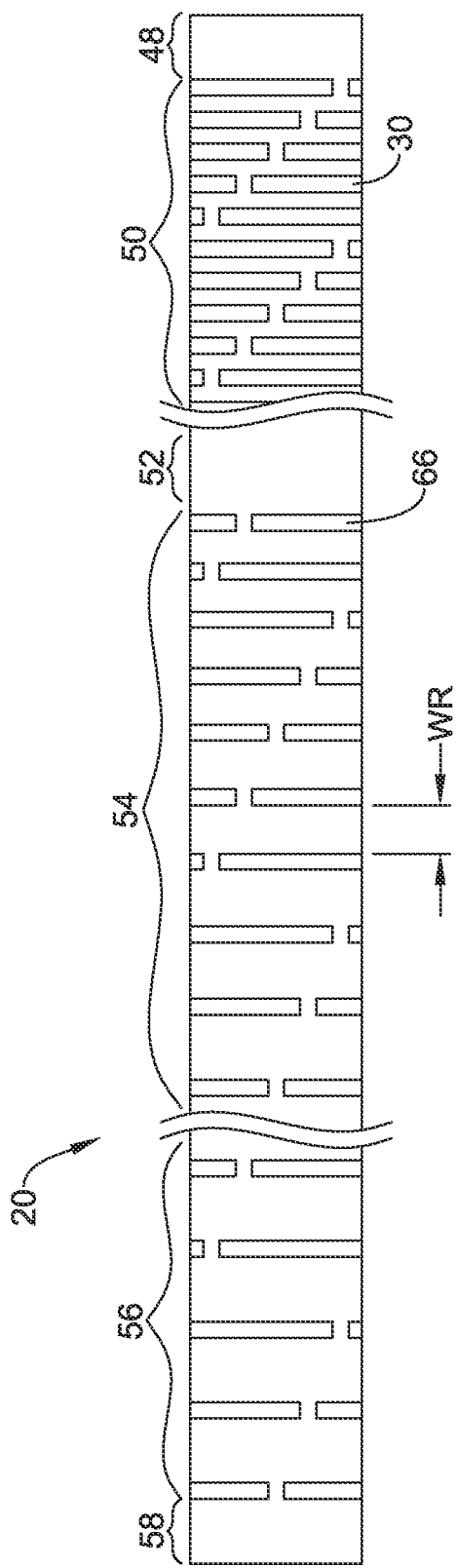
FIG. 6 is a side view of example tubular member.

The structure of tubular member 20 may vary in a number of different ways so as to provide the desired flexural rigidity (e.g., the desired flexural rigidity along at least a portion of tubular member 20 that varies as a function of a fourth power polynomial). FIG. 6 illustrates tubular member 20 showing slots 30 formed therein and arranged in a pattern that may provide the desired flexural rigidity. For example, tubular member 20 may have a distal uncut or non-slotted section 48 disposed at the distal end of tubular member 20. Section 48 may lack slots 30 and may have a length in the range of about 0.01 to 0.1 inches, or about 0.02 to 0.03 inches, or about 0.024 inches.

Next to section 48 may be a distal slotted section 50 where slots 30 have an essentially constant spacing. Section 48 may have a length in the range of about 0.1 to 5 inches, or about 0.1 to 1 inches, or about 0.4 to 0.6 inches, or about 0.49 inches. The flexural rigidity of section 50 may also be essentially constant. For example, the flexural rigidity of section 50 may be in the range of about $1\times10^{-6}$ to $9\times10^{-5}$ lbs-inches$^2$, or about $5\times10^{-6}$ to $3\times10^{-5}$ lbs-inches$^2$, or about $6\times10^{-6}$ to $2.1\times10^{-5}$ lbs-inches$^2$. In one example, the flexural rigidity of section 50 may be about $6\times10^{-6}$ lbs-inches$^2$. In another example, the flexural rigidity of section may be about $2.1\times10^{-5}$ lbs-inches$^2$.

Tubular member 20 may also include a mid-distal uncut or non-slotted section 52. Section 52 may lack slots 30 and may have a length in the range of about 0.001 to 0.1 inches, or about 0.01 to 0.02 inches, or about 0.012 inches. Tubular member 20 may also include a transition section 54 that is disposed adjacent to section 52. The spacing of slots 30 in transition section 54 may vary so as to provide section 50 with a flexural rigidity that is a function of a third order to a fifth order equation (e.g., may be a function of a third order to a fifth order polynomial). For example, transition section 54 may have a transition in flexural rigidity that varies as a function of a fourth power polynomial. Section 54 may have a length in the range of about 1 to 5 inches, or about 1 to 4 inches, or about 1 to 3 inches, or about 2.49 inches.

Tubular member 20 may also include a proximal slotted section 56 where slots 30 have an essentially constant spacing. Section 56 may have a length in the range of about 0.1 to 10 inches, or about 2 to 8 inches, or about 3 to 5 inches, or about 3.95 to 4.25 inches. The flexural rigidity of section 56 may also be essentially constant. For example, the flexural rigidity of section 56 may be in the range of about $1\times10^{-4}$ to $9\times10^{-3}$ lbs-inches$^2$, or about $1\times10^{-3}$ to $5\times10^{-3}$ lbs-inches$^2$, or about $1\times10^{-3}$ to $3\times10^{-3}$ lbs-inches$^2$, or about $1.42\times10^{-3}$ to $2.64\times10^{-3}$ lbs-inches$^2$. Next to section 56 may be a proximal uncut section 58, which may lack slots 30 and may have a length in the range of about 0.01 to 0.1 inches, or about 0.02 to 0.04 inches, or about 0.03 inches.

It can be appreciated that the above description of tubular member 20 is provided as an example. Numerous alternative tubular members are contemplated that may lack one or more of the sections described above, include other sections having similar or different properties, or include other structural features.

As indicated above, the flexural rigidity of section 54 may vary. In some embodiments, the flexural rigidity of section 54 may be a function of a third to a fifth order polynomial. For example, the flexural rigidity of section 54 may be a function of a fourth power polynomial [e.g., $FR(x)=A+Bx^4$]. In some embodiments, the flexural rigidity of section 54 ($FR_{54}$) may transition from the flexural rigidity of section 50 ($FR_{50}$) to that of section 56 ($FR_{56}$). For example, the flexural rigidity of section 54 ($FR_{54}$) may vary according to the following equation, where x is the position along the longitudinal axis of tubular member 20, $x_s$ is the distance from the distal end of tubular member 20 to the distal end of section 54, $x_f$ is the distance from the distal end of the tubular member 20 to the proximal end of section 54, $(x_f-x_s)$ is the length of section 54, and where the relative position within section 54 is $(x-x_s)$:

$$FR_{54} = FR_{50} + [(FR_{56} - FR_{50})/\{(x_f - x_s)^4\}] * (x - x_s)^4$$
$$= FR_{50} + (FR_{56} - FR_{50}) * \{(x - x_s)/(x_f - x_s)\}^4$$

This is just an example. Other equations are contemplated that may provide tubular member 20 with the desired flexural rigidity.

Although the above discussion of the flexural rigidity of section 54 is described as being a function of a third order to a fifth order polynomial (e.g., a fourth power equation or polynomial), this is not intended to be limiting. For example, the entire length of tubular member 20 may have a flexural rigidity that varies according to a third order to a fifth order polynomial (e.g., a fourth power equation or polynomial) or any one or more of the sections of tubular member 20 may vary in flexural rigidity in this or any other manner.

Forming tubular member 20 with the desired fourth power transition in flexural rigidity along a portion or all of its length may include a number of procedural steps. For example, these steps may include providing or otherwise starting with a tube having a known inside diameter, a known outside diameter, and that is made from a known material (e.g., having a known Young's modulus). The design may then include setting a constant ratio of the beam height to ring width or the selection of a range of beam height to ring width ratios. The term "beam height" generally refers to the length or width of the beam in the radial direction. The term "ring width" generally refers to the length between two adjacent slots 30 and an example of ring width, $W_r$, is shown in FIG. 6.

The beam height to ring width ratio may be set at a value of about 0.5 to 5, or about 1 to 2, or about 1.3 to 1.7, or at a number of individual values over these ranges. With these parameters set, sample parts can be made to establish a "flexural rigidity profile". For example, one sample part may be made with essentially "shallow" cuts (e.g., the beam height may be relatively high). This sample may represent a "stiff" sample tube or a tube with a relatively high flexural rigidity. A number of distinct samples may also be made with shallow cuts, using a number of different beam height to ring width ratios. Other sample parts may also be made including a part with essentially "deep" cuts (e.g., the beam height may be relatively low, which may result in a more flexible tube or a tube with a relatively low flexural rigidity), again using a number of different beam height to ring width ratios, and a number of intermediate tubes that fall intermediate (in terms of beam height) between the first two parts may also be made. The intermediate parts may also be made with a number of different beam height to ring width ratios.

The flexural rigidity can then be measured in the sample parts. Using available software (e.g., EXCEL®, available from Microsoft Corporation, Redmond, Wash.; DESIGN EXPERT, available from Stat Ease, Minneapolis, Minn.), the measured flexural rigidities, beam heights, and beam height to ring width ratios can be entered into a "designed experiment", which can then generate equations that relate flexural rigidity to beam height, ring width, and beam height to ring width ratio. As an alternative to making physical samples, techniques such as mathematical modeling (e.g., Finite Element Analysis, etc.) can be used to simulate physical samples, and theoretical flexural rigidities can be calculated. This information can be entered into a "designed experiment", as above. If desired, a number of physical samples could be made and measured with respect to flexural rigidity, to confirm and/or correct the accuracy of the mathematical simulation. For the purposes of this disclosure, the equations resulting from the designed experiment will be termed the "mathematical model".

With the known parameters set (e.g., starting flexural rigidity, ending flexural rigidity, and ratio or range of ratios of beam height to ring width), a cut pattern can be established with the desired transition in flexural rigidity (e.g., transitioning as a function of a fourth power equation). If the beam height to ring width ratio is not constant, the mathematical model may include one or more equations that describe the change in the ratio as a function of distance from a starting point (e.g., the starting point at which a transition in beam height to ring width ratio begins). This function may be linear, squared, cubed, polynomial, etc. The mathematical model can be used to determine the beam height (or cut depth) and ring width needed to achieve a flexural rigidity at the start of the transition that is equal to the starting flexural rigidity, using the ratio of beam height to ring width defined by the equation noted above. Because the ring width is equal to the distance between cuts minus the width or kerf of the cutting instrument (e.g., and/or the width of the cut), the distance that the tube is translated relative to the cutting apparatus can be readily determined.

Next, the fourth power equation can be used to calculate what the flexural rigidity should be at the second cut point. Once this value is known, the mathematical model can be used to calculate the particular beam height and ring width that provides the calculated flexural rigidity. Once a cut is made to define the particular beam height, the process can be repeated (e.g., translate the tube the proper distance that is consistent with the beam height to ring width ratio, calculate the flexural rigidity at the next cut location using the fourth power equation, and using the mathematical model to calculate what beam height will give the calculated flexural rigidity) until the full length of the tube for which the desired transition spans is cut in the desired manner.

Figure 7:
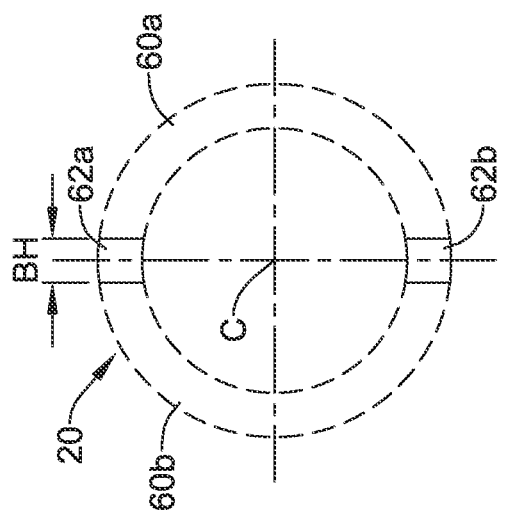
FIG. 7 is a cross-sectional view of a portion of an example tubular member.
Figure 8:
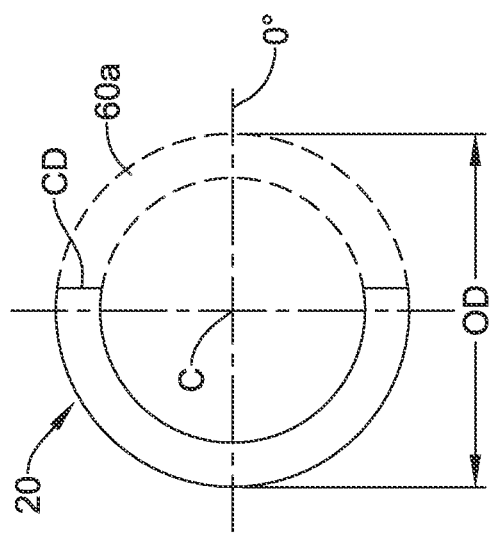
FIG. 8 is another cross-sectional view of a portion of an example tubular member.
Figure 9:
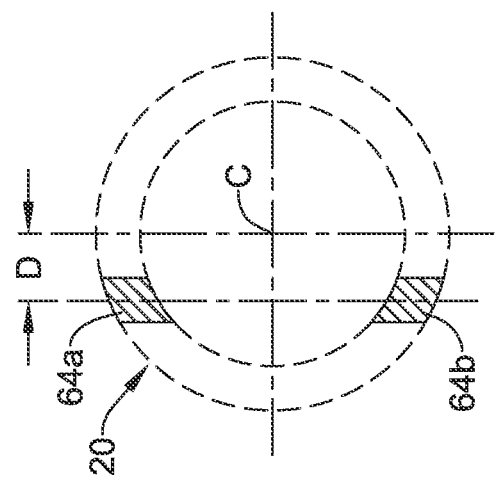
FIG. 9 is another cross-sectional view of a portion of an example tubular member.

FIGS. 7-9 depict a variety of example cross-sectional views taken through different portions of tubular member 20 and cuts formed in tubular member 20 in order to illustrate some additional variations contemplated for the distribution or arrangement of slots 30 in tubular member 20. The description of these figures make use of the words "beam" and/or "beams". The beams are the portion of tubular member 20, often resembling a beam in appearance, that remains after cutting away a portion of tubular member 20 to form slots 30.

Turning now to FIG. 7, when a suitable cutting apparatus cuts into tubular member 20 to form slots 30, the cutting apparatus cuts through tubular member 20 at a particular angular position (e.g., for convenience sake assume the angular position is located at the right hand side or the 0° position of tubular member 20) to a position called the cut depth CD and defines a slot 60a (depicted in phantom as the portion of tubular member 20 removed by cutting). In this example, the beam height BH is the length of width of the beam in the radial direction. The beam height BH may be related to the cut depth CD and the outer diameter OD of tubular member 20. For example, in at least some cases the "deeper" the cut depth CD, the "shorter" the beam height BH. In fact, the relationship between cut depth CD and beam height BH can be represented by the equation:

$$CD=0.5*(OD-BH)$$

Another cut 60b may be made in tubular member 20 at the same longitudinal position (e.g., from the opposite angular position (e.g., 180°)) of tubular member 20 as shown in FIG. 8. Here it can be seen that a pair of beams 62a/62b is defined.

Along the length of tubular member 20, additional pairs of slots and beams can be formed by making additional cuts. In some embodiments, the cuts can be from the same position (e.g., from the 0° and the 180° positions of tubular member 20). Alternatively, the cuts can begin from a different angular position. For example, the first cut made in tubular member 20 at a subsequent longitudinal position may be rotated a radial distance or angle A from where the first cut was made at the first longitudinal position. Angle A could be a suitable angle such as, for example, about 60 to 120°, or about 75 to 100°, or about 85°. Another cut from the opposite side of tubular member 20 defines a second pair of beams. At other longitudinal positions, cuts can be rotated to the same extent or to different extents.

It can be appreciated that the beam pairs (e.g., beam pairs 62a/62b) may have centers that align with the tube centerline C (i.e., a line drawn between the middle of opposing pairs of beams goes through the tube centerline C). While this can be desirable in some embodiments, other arrangements are contemplated that include beam centers that are offset from the tube centerline C. For example, FIG. 9 depicts a portion of tubular member 20 where beam pairs 64a/64b are offset a distance D from the tube centerline C.

In at least some embodiments, one or more sections of tubular member 20 may include beam pairs that are offset from the tube centerline C. For example, section 50 may include any number of slots 30 (e.g., one, some, or all) that include beams that are offset from the tube centerline C. In some embodiments, all of the slots 30 are offset from the tube centerline C the same distance. This distance may be about 0.001 to 0.007 inches, or about 0.002 to 0.004 inches, or about 0.003 inches. In other embodiments, the distance that the beams are offset may vary.

Other sections of tubular member 20 may have the same amount of offset (e.g., the distance that the beams are offset from the tube centerline C is the same), a different amount of offset, or a variable amount of offset. For example, in section 54, the offset or distance that the beams are offset from the tube centerline C at or near the distal end of section 54 (e.g., at a first slot which is labeled with reference number 66 in FIG. 6) may be the same as the amount of offset in section 50. Over a number of slots or a distance, the amount of offset may gradually reduce to zero. This transition may occur over a distance of about 0.1 to 1 inches, or about 0.2 to 0.5 inches, or about 0.25 inches. Other distances are contemplated. Other sections or portions of sections of tubular member 20 may also have offsets that are the same or different from those in sections 50/54, or may have different amounts of offset altogether.

The amount of beam offset in section 54 may linearly transition to zero offset (e.g., beams aligned with the tube centerline C). This linear transition may be defined by the following relationship:

$$\text{Offset}(x)=0.003*(1-x/0.25)$$

where:
Offset is the distance from the tube centerline C that the beams are offset,
x is the distance from the start of section 54.

In addition to variation in offset, other variations are contemplated. For example, the distance between adjacent slots 30 may be termed the ring width $W_r$ as shown in FIG. 6. A ratio may be established between the beam height BH and the ring width $W_r$. In some embodiments, this ratio may be constant in one or more portions of the entire length of tubular member 20. Alternatively, the ratio of the beam height BH and the ring width $W_r$ may vary. For example, the ratio of the beam height BH and the ring width $W_r$ may vary in section 54. This may include any suitable variation. In some embodiments, the ratio of the beam height BH and the ring width $W_r$ may vary such that the ratio at the proximal end of section 54 is greater than at the distal end. Other variations are contemplated.

In one example, the ratio of the beam height to ring width is constant in section 50 and remains constant over a distal portion of section 54. At a distance of about 0.1 to 3 inches, or about 1 to 3 inches, or about 1.95 to 2.25 inches, or about 1.97 to 2.12 inches, the ratio of the beam height to ring width may begin to vary. For example, the beam height to ring width ratio in section 50 may be about 1 to 3, about 1 to 2, about 1 to 1.7, about 1.2 to 1.5, or about 1.3. The same may be true of the distal portion of section 54. The beam height to ring width ratio may then vary over a length of section 54. The transition may be a linear transition (e.g., the beam height to ring width ratio increases linearly) over a length of about 0.1 to 1 inches, about 0.25 to 1 inches, about 0.3 to 0.6 inches, about 0.38 to 0.53 inches, or otherwise a distance sufficient to extend to the proximal end of section 54. The beam height to ring width ratio at the end of the transition may be about 1 to 2, about 1.3 to 1.8, or about 1.6 to 1.7.

Various embodiments of arrangements and configurations of slots 30 are contemplated that may be used in addition to what is described above or may be used in alternate embodiments. For example, in some embodiments, at least some, if not all of slots 30 are disposed at the same or a similar angle with respect to the longitudinal axis of tubular member 20. As shown, slots 30 can be disposed at an angle that is perpendicular, or substantially perpendicular, and/or can be characterized as being disposed in a plane that is normal to the longitudinal axis of tubular member 20. However, in other embodiments, slots 30 can be disposed at an angle that is not perpendicular, and/or can be characterized as being disposed in a plane that is not normal to the longitudinal axis of tubular member 20. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 20 while still allowing for suitable torque transmission characteristics. Slots 30 may be formed such that one or more rings and/or tube segments interconnected by one or more segments and/or beams that are formed in tubular member 20, and such tube segments and beams may include portions of tubular member 20 that remain after slots 30 are formed in the body of tubular member 20. Such an interconnected structure may act to maintain a relatively high degree of torsional stiffness, while maintaining a desired level of lateral flexibility. In some embodiments, some adjacent slots 30 can be formed such that they include portions that overlap with each other about the circumference of tubular member 20. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 20 to achieve desired properties. For example, adjacent slots 30, or groups of slots 30, can be arranged in a symmetrical pattern, such as being disposed essentially equally on opposite sides about the circumference of tubular member 20, or can be rotated by an angle relative to each other about the axis of tubular member 20. Additionally, adjacent slots 30, or groups of slots 30, may be equally spaced along the length of tubular member 20, or can be arranged in an increasing or decreasing density pattern, or can be arranged in a non-symmetric or irregular pattern. Other characteristics, such as slot size, slot shape, and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section, or a distal section, or the entire tubular member 20, may not include any such slots 30.

As suggested herein, slots 30 may be formed in groups of two, three, four, five, or more slots 30, which may be located at substantially the same location along the axis of tubular member 20. Alternatively, a single slot 30 may be disposed at some or all of these locations. Within the groups of slots 30, there may be included slots 30 that are equal in size (i.e., span the same circumferential distance around tubular member 20). In some of these as well as other embodiments, at least some slots 30 in a group are unequal in size (i.e., span a different circumferential distance around tubular member 20). Longitudinally adjacent groups of slots 30 may have the same or different configurations. For example, some embodiments of tubular member 20 include slots 30 that are equal in size in a first group and then unequally sized in an adjacent group. It can be appreciated that in groups that have two slots 30 that are equal in size and are symmetrically disposed around the tube circumference, the centroid of the pair of beams (i.e., the portion of tubular member 20 remaining after slots 30 are formed therein) is coincident with the central axis of tubular member 20. Conversely, in groups that have two slots 30 that are unequal in size and whose centroids are directly opposed on the tube circumference, the centroid of the pair of beams can be offset from the central axis of tubular member 20. Some embodiments of tubular member 20 include only slot groups with centroids that are coincident with the central axis of the tubular member 20, only slot groups with centroids that are offset from the central axis of tubular member 20, or slot groups with centroids that are coincident with the central axis of tubular member 20 in a first group and offset from the central axis of tubular member 20 in another group. The amount of offset may vary depending on the depth (or length) of slots 30 and can include other suitable distances.

Slots 30 can be formed by methods such as micro-machining, saw-cutting (e.g., using a diamond grit embedded semi-conductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 30 in tubular member 20 using these or other manufacturing steps.

In at least some embodiments, slots 30 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow tubular member 20 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form tubular member 20 without being limited by a minimum cutting blade size. Consequently, tubular members 20 may be fabricated for use in neurological devices or other devices where a relatively small size may be desired.

The materials that can be used for the various components of guidewire 10 (and/or other guidewires disclosed herein) and the various tubular members disclosed herein may include those commonly associated with medical devices. For simplicity purposes, the following discussion makes reference to tubular member 20 and other components of guidewire 10. However, this is not intended to limit the devices and methods described herein, as the discussion may be applied to other similar tubular members and/or components of tubular members or devices disclosed herein.

Tubular member 20 and/or other components of guidewire 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, to enhance compatibility with MRI machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (i.e., gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example, materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using a suitable connecting technique and/or with a connector. For example, the different portions of core wire 18 can be connected using welding (including laser welding), soldering, brazing, adhesive, or the like, or combinations thereof. These techniques can be utilized regardless of whether or not a connector is utilized. The connector may include a structure generally suitable for connecting portions of a guidewire. One example of a suitable structure includes a structure such as a hypotube or a coiled wire which has an inside diameter sized appropriately to receive and connect to the ends of the proximal portion and the distal portion. Other suitable configurations and/or structures can be utilized for connector 26 including those connectors described in U.S. Pat. Nos. 6,918,882 and 7,071,197 and/or in U.S. Patent Pub. No. 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The disclosures of U.S. Patent Application Publication Nos. US 2009/0118675, US 2009/0254000, and US 2009/0177185, the entire disclosures of which are herein incorporated by reference, may pertain to this disclosure. The disclosure of U.S. Pat. No. 6,106,488, the entire disclosure of which is herein incorporated by reference, may also pertain to this disclosure.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A catheter, comprising:
a tubular member having a longitudinal axis and having a lumen defined therein;
wherein the tubular member has a plurality of slots formed therein;
wherein the tubular member includes a variably spaced slot section that has a flexural rigidity that varies from a first flexural rigidity to a second flexural rigidity, and wherein the transition from the first flexural rigidity to the second flexural rigidity is a function of a fourth order equation;
wherein the first flexural rigidity is in the range of about $1 \times 10^{-6}$ to about $9 \times 10^{-5}$ lbs-inches$^2$; and wherein the second flexural rigidity is in the range of about $1\times10^{-3}$ to about $5\times10^{-3}$ lbs-inches$^2$.

2. The catheter of claim 1, wherein the second flexural rigidity is in the range of about $1\times10^{-3}$ to about $3\times10^{-3}$ lbs-inches$^2$.

3. The catheter of claim 1, wherein the second flexural rigidity is in the range of about $1.42\times10^{-3}$ to about $2.64\times10^{-3}$ lbs-inches$^2$.

4. The catheter of claim 1, wherein the tubular member has a distal end and wherein the tubular member includes a first non-slotted section disposed at the distal end, the first non-slotted section being free of slots.

5. The catheter of claim 4, wherein the tubular member includes a first constantly spaced slot section that includes slots that have a constant spacing along the longitudinal axis, the first constantly spaced slot section being disposed adjacent to the first non-slotted section.

6. The catheter of claim 5, wherein the tubular member includes a second constantly spaced slot section that includes slots that have a constant spacing along the longitudinal axis.

7. The catheter of claim 6, wherein the variably spaced slot section is disposed between the first constantly spaced slot section and the second constantly spaced slot section.

8. The catheter of claim 7, wherein the tubular member includes a second non-slotted section disposed between the first constantly spaced slot section and the variably spaced slot section, the second non-slotted section being free of slots.

9. The catheter of claim 8, wherein the tubular member has a proximal end and wherein the tubular member includes a third non-slotted section disposed at the proximal end, the third non-slotted section being free of slots.

10. The catheter of claim 1, wherein the slots define a beam height for a pair of beams at a longitudinal position along the tubular member, wherein a distance between two longitudinally adjacent slots defines a ring width, and wherein the ratio of the beam height to ring width is constant along at least a portion of the tubular member.

11. The catheter of claim 10, wherein the ratio of beam height to ring width is constant in a first portion of the tubular member and wherein the ratio of beam height to ring width varies in a second portion of the tubular member.

12. The catheter of claim 11, wherein the ratio of beam height to ring width varies along the variably spaced slot section.

13. The catheter of claim 1, wherein the slots define beams in the tubular member and wherein at least some of the beams are offset from a centerline of the tubular member.

14. The catheter of claim 13, wherein the beams are aligned with the centerline along a portion of the tubular member and wherein the beams are offset from the centerline along a second portion of the tubular member.

15. The catheter of claim 14, wherein the variably spaced slot section includes beams that are offset a distance from the centerline of the tubular member.

16. The catheter of claim 15, wherein the variable spaced slot section includes a transition where the beams that are offset from the centerline transition from being offset by the distance to the beams that are aligned with the centerline of the tubular member.

17. A catheter, comprising:
a super-elastic nickel-titanium tubular member having a longitudinal axis and having a lumen defined therein;
wherein the tubular member has a plurality of slots formed therein;
wherein the tubular member includes a variably spaced slot section that has a flexural rigidity that varies from a first flexural rigidity to a second flexural rigidity, and wherein the transition from the first flexural rigidity to the second flexural rigidity is a function of a fourth order equation;
wherein the first flexural rigidity is in the range of about $1\times10^{-6}$ to about $9\times10^{-5}$ lbs-inches$^2$; and
wherein the second flexural rigidity is in the range of about $1\times10^{-3}$ to about $5\times10^{-3}$ lbs-inches$^2$.

18. The catheter of claim 17, wherein the tubular member includes a first constantly spaced slot section and a second constantly spaced slot section that each include slots that are spaced a constant distance along the longitudinal axis.

19. The catheter of claim 18, wherein the variably spaced slot section is disposed between the first constantly spaced slot section and the second constantly spaced slot section.

20. A method for manufacturing a catheter, comprising:
forming a first slot in a tubular member at a first position along a longitudinal axis of the tubular member;
forming a second slot in the tubular member at a second position along the longitudinal axis;
forming a plurality of additional slots in the tubular member at a plurality of positions along the longitudinal axis; and
wherein the first slot, the second slot, and the plurality of additional slots are variably spaced along the longitudinal axis so as to define a variably spaced slot section wherein the tubular member includes a variably spaced slot section that has a flexural rigidity that varies from a first flexural rigidity to a second flexural rigidity, wherein the transition from the first flexural rigidity to the second flexural rigidity is a function of a fourth order equation, wherein the first flexural rigidity is in the range of about $1\times10^{-6}$ to about $9\times10^{-5}$ lbs-inches$^2$, and wherein the second flexural rigidity is in the range of about $1\times10^{-3}$ to about $5\times10^{-3}$ lbs-inches$^2$.

* * * * *

UNITED STATES PATENT AND TRADEMARK OFFICE
CERTIFICATE OF CORRECTION

PATENT NO. : 8,784,337 B2  
APPLICATION NO. : 14/048852  
DATED : July 22, 2014  
INVENTOR(S) : Voeller et al.

Page 1 of 1

It is certified that error appears in the above-identified patent and that said Letters Patent is hereby corrected as shown below:

In the Specification

Column 13  
Line 62: before ") to about 120°C", delete "."  
Line 62: after "to about 120°C", delete "."

Signed and Sealed this  
Thirtieth Day of September, 2014

Michelle K. Lee  
*Deputy Director of the United States Patent and Trademark Office*